(12) United States Patent
Vo-Dinh et al.

(10) Patent No.: US 6,212,421 B1
(45) Date of Patent: Apr. 3, 2001

(54) METHOD AND APPARATUS OF SPECTRO-ACOUSTICALLY ENHANCED ULTRASONIC DETECTION FOR DIAGNOSTICS

(75) Inventors: Tuan Vo-Dinh, Knoxville, TN (US); Stephen J. Norton, Raleigh, NC (US)

(73) Assignee: Lockheed Martin Energy Research Corp., Oak Ridge, TN (US)

( * ) Notice: Subject to any disclaimer, the term of this patent is extended or adjusted under 35 U.S.C. 154(b) by 0 days.

(21) Appl. No.: 09/390,132

(22) Filed: Sep. 3, 1999

(51) Int. Cl.[7] .................................. A61B 5/00; A61B 8/00
(52) U.S. Cl. ........................ 600/407; 600/437; 600/443
(58) Field of Search ..................................... 600/407, 473, 600/476, 437, 438, 459, 443, 447; 601/3, 4; 606/2, 3; 73/587, 596; 367/7

(56) References Cited

U.S. PATENT DOCUMENTS

| | | | | |
|---|---|---|---|---|
| 4,059,010 | * | 11/1977 | Sachs ....................................... | 73/596 |
| 5,713,356 | * | 2/1998 | Kruger ................................... | 600/407 |
| 5,924,986 | * | 7/1999 | Chandler et al. ...................... | 600/407 |
| 6,102,857 | * | 8/2000 | Kruger ................................... | 600/437 |
| 6,104,942 | * | 8/2000 | Kruger ................................... | 600/407 |

* cited by examiner

Primary Examiner—Marvin M. Lateef
Assistant Examiner—Ali M. Imam
(74) Attorney, Agent, or Firm—Needle & Rosenberg, P.C.

(57) ABSTRACT

An apparatus for detecting a discontinuity in a material includes a source of electromagnetic radiation has a wavelength and an intensity sufficient to induce an enhancement in contrast between a manifestation of an acoustic property in the material and of the acoustic property in the discontinuity, as compared to when the material is not irradiated by the electromagnetic radiation. An acoustic emitter directs acoustic waves to the discontinuity in the material. The acoustic waves have a sensitivity to the acoustic property. An acoustic receiver receives the acoustic waves generated by the acoustic emitter after the acoustic waves have interacted with the material and the discontinuity. The acoustic receiver also generates a signal representative of the acoustic waves received by the acoustic receiver. A processor, in communication with the acoustic receiver and responsive to the signal generated by the acoustic receiver, is programmed to generate informational output about the discontinuity based on the signal generated by the acoustic receiver.

34 Claims, 2 Drawing Sheets

METHOD AND APPARATUS OF SPECTRO-ACOUSTICALLY ENHANCED ULTRASONIC DETECTION FOR DIAGNOSTICS

STATEMENT REGARDING FEDERALLY SPONSORED RESEARCH

This invention was made with government support under Contract No. DE-AC05-96OR22464 awarded by Department of Energy to Lockdeed Martin Energy Research Corp. The government has certain rights in the invention.

BACKGROUND OF THE INVENTION

1. Field of the Invention

The present invention relates to ultrasonic detection and, more specifically, to a device for enhancing ultrasonic detection.

2. Description of the Prior Art

Currently, the most common method of diagnosing breast cancer is X-ray mammography. Although it is often effective, it uses ionizing radiation, which has an inherent risk to the tissues being examined. Ultrasound detection is also used in breast examination. Ultrasound detection is based on differences in sound velocity in normal and abnormal tissues. However, it has a low probability of detecting many non-palpable tumors. Magnetic resonance imaging has also been used, but requires sophisticated and expensive equipment.

Exposing materials such as tissues to electromagnetic radiation causes the tissues to exhibit changes in acoustic properties as a result of photonic absorption and subsequent local heating. Spectrochemical techniques such as laser-induced fluorescence have previously been used to detect malignant tumors in vivo (see, e.g., U.S. Pat. No. 5,579,773, the disclosure of which is incorporated herein by reference). Certain tissues, such as tumors, exhibit greater changes in acoustic properties than in surrounding tissues. It has also been discovered that exposing tissues to modulated or pulsed light may also cause the generation of acoustic waves in the tissue, a process often referred to as the photo-acoustic effect. In photo-acoustic detection, intensity-modulated light or pulsed light is allowed to diffuse into a specimen and photons are absorbed, inducing energy level transitions in chemical and biological compounds. When the energy levels return to their de-excited ground state, some of the energy is transformed into kinetic energy or heat. The intensity modulation of the incident radiation produces a coherent modulation of the temperature of the material that, due to thermal expansion, generates a periodic pressure fluctuation of the same frequency. This pressure fluctuation, or acoustic signal, can be detected with a microphone or transducer in contact with the material being examined.

Photo-acoustic spectroscopy has been successfully performed on a variety of biological materials (see, e.g., Rosencwaig, A., *Photo-acolistics and Photo-acotistic Spectroscopy*, Wiley, New York, 1980). Studies of whole blood have been performed, in which conventional absorption spectroscopy has failed due to excessive light scattering. Other examples include: Photo-acoustic spectroscopy of chlorophyll within the intact green leaf and the detection of plant pathology; analysis of the biochemical characteristics of marine algae and phytoplankton and studies of the photochemical mechanisms of these organisms; the monitoring of bacteria in various stages of development; the effect of different commercial sun screens on human epidermal tissue; studies of human eye cataracts, and the detection of protein structural changes in rat epidermal tissue during postpartum maturation.

Many conventional analytical techniques (e.g., chromatography, fluorometry, spectrophotometry) are effective when applied to solutions of extracted biochemical compounds, Photo-acoustic spectroscopy has been shown to be effective in the biochemical characterization of intact and complex biological systems, such as intact cells and tissues.

SUMMARY OF THE INVENTION

This invention involves non-invasive methods and instruments for improved chemical, environmental and biomedical diagnosis using an approach based on spectro-acoustically enhanced ultrasonic detection. The combination of both ultrasonic and laser photo-acoustic methods, which is aimed at providing physical as well as spectrochemical properties of constituents of materials, will significantly extend the diagnostic applicability. This invention will greatly improve measurements of ultrasonic waves using a combination of detection approaches and probe/detector geometries. The combination of both ultrasonic and laser photo-acoustic methods will significantly extend the diagnostic efficiency and applicability for diagnosis. The basic principle of this invention is the integration of the following combination of techniques: (a) laser optical/photo-acoustic excitation, carrying the spectrochemical and electronic/molecular properties of biological constituents of tissues; (b) ultrasonic detection containing spatial information, and the physical and mechanical properties of tissues; and (c) modulation and synchronized detection used to improve the signal-to-noise ratio of detection to achieve improved sensitivity.

The disadvantages of the prior art are overcome by the present invention which, in one aspect, is an apparatus for detecting a discontinuity in a material, in which a source of electromagnetic radiation has a wavelength and an intensity sufficient to induce an enhancement in contrast between a manifestation of an acoustic property in the material and of the acoustic property in the discontinuity, as compared to when the material is not irradiated by the electromagnetic radiation. An acoustic emitter directs acoustic waves to the discontinuity in the material. The acoustic waves have a sensitivity to the acoustic property. An acoustic receiver receives the acoustic waves generated by the acoustic emitter after the acoustic waves have interacted with the material and the discontinuity. The acoustic receiver also generates a signal representative of the acoustic waves received by the acoustic receiver. A processor, in communication with the acoustic receiver and responsive to the signal generated by the acoustic receiver, is programmed to generate informational output about the discontinuity based on the signal generated by the acoustic receiver.

In another aspect, the invention is an apparatus for detecting a mass, having a density, in a tissue, having a density. An electromagnetic radiation source directs a beam of electromagnetic radiation into the tissue toward the mass. The beam has a wavelength and intensity sufficient to induce an enhancement in contrast between the density of the mass relative to the density of the tissue. An ultrasound transmitter directs ultrasound waves into the tissue toward the mass. An ultrasound receiver receives ultrasound waves that have interacted with the tissue and the mass. A processor, responsive to the ultrasound receiver, detects the mass based on the ultrasound waves received by the ultrasound receiver.

In yet another aspect, the invention is a method of detecting a discontinuity in a material. The material is irradiated with a beam of electromagnetic radiation having an energy and an intensity sufficient to induce an enhancement in contrast between a manifestation of an acoustic property in the material and of the acoustic property in the discontinuity, as compared the contrast when the material is not irradiated by the beam. This enhanced contrast is due to the difference in the spectrochemical properties of the material and the discontinuity. The material is irradiated with acoustic waves so that acoustic energy interacts with the material and the discontinuity. Waves that have interacted with the material and the discontinuity are received. An informational output about the discontinuity based on the received waves that have interacted with the material and the discontinuity is generated.

In yet another aspect, the invention is a method of detecting a mass in a tissue. The tissue is irradiated with a beam of electromagnetic radiation having an energy and an intensity sufficient to induce an enhancement in contrast between a manifestation of an acoustic property in the tissue and of the acoustic property in the mass, as compared the contrast when the tissue is not irradiated by the beam. The tissue is also irradiated with acoustic waves so that acoustic energy interacts with the tissue and the mass. Waves that have interacted with the tissue and the mass are received. An informational output about the mass based on the received waves that have interacted with the tissue and the mass is generated.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
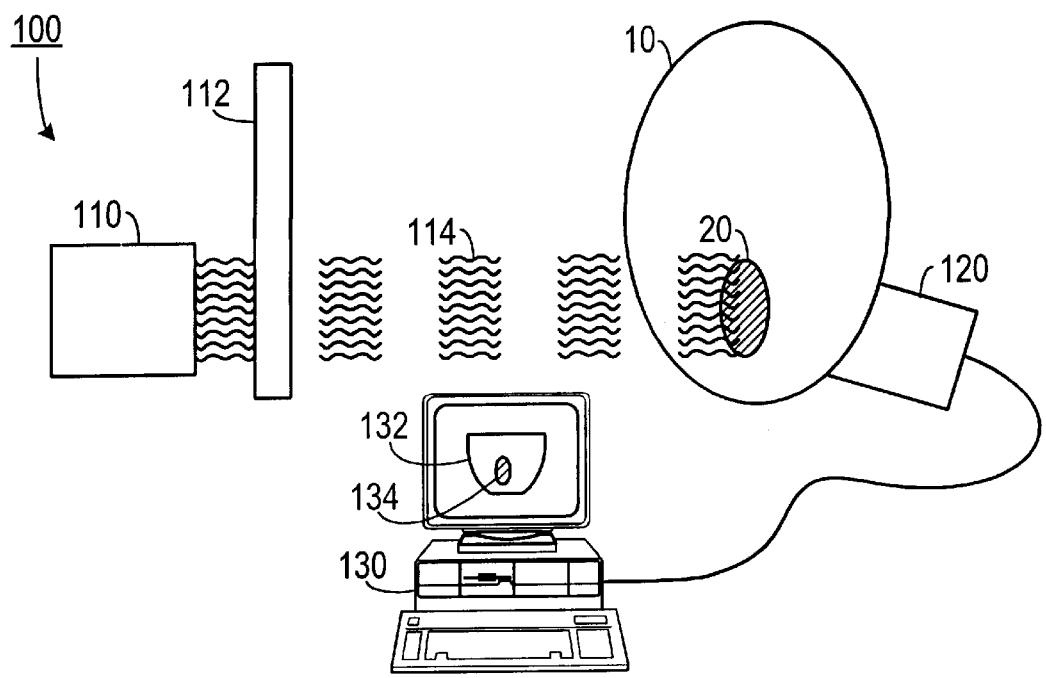
FIG. 1 is a schematic diagram of one embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Ultrasonic detection method is based on the differences in sound velocity in the mass and the discontinuity. For example, in medical diagnostics, the mass is the normal tissue and the discontinuity is the tumor under investigation. The ultrasound technique alone carries information on the physical and mechanical properties of tissues. On the other hand, the photo-acoustic technique is based on the spectrochemical and electronic/molecular properties of tissue constituents. In the photo-acoustic method can be summarized as follows, intensity-modulated monochromatic light is allowed to diffuse into the specimen (e.g., breast tissue), whereupon photons are absorbed, inducing energy level transitions in biochemical compounds. When these levels return to their ground state (de-excitation), some of the energy is transformed into kinetic energy or heat. The intensity modulation of the incident radiation in turn produces a coherent modulation of the temperature of the material which, due to thermal expansion, generates a periodic pressure fluctuation at the same frequency. This fluctuation, or acoustic signal, can be detected with high sensitivity with a microphone (for gas coupling to the material) or by a piezoelectric transducer in direct contact with the material. When the laser light beam is used to produce Photo-acoustic signals in conjunction with an ultrasonic emitter/receiver, the resulting effect is a modulation of the ultrasonic response caused by the Photo-acoustic effect on the local environments. For example, in biomedical diagnostics, as a result of this combined effect, detection of the tumor could be improved not only through the detection of slight changes in density, temperature or thermal diffusivity due to the vascularization that often accompanies breast tumors, but also by virtue of differences in spectrochemical properties of constituents, and biochemical changes affecting energy level de-excitation rates.

As shown in FIG. 1, one embodiment of the invention employs an apparatus 100 for enhancing acoustic detection of a discontinuity 20 in a material 10. The material 10 could include any object in which acoustic detection is used to detect discontinuities. For example, the material 10 could be living tissue and the discontinuity 20 could be a mass within the tissue. The apparatus employs a source 110 of electromagnetic energy, which could include optical energy or non-optical (e.g. ultraviolet, infrared, near-infrared, X-ray, or microwave) energy. A typical source 110 for optical energy would be a laser, which would typically be collimated. The electromagnetic energy is of a type so that it may penetrate to an area within the material 10 wherein a discontinuity 20 is likely to exist. The electromagnetic energy must have a wavelength (or other indicia of energy) and an intensity sufficient to induce an enhancement in contrast between a manifestation of an acoustic property in the material 10 and of the acoustic property in the discontinuity 20.

The type of energy transitions produced in the specimen depends on the energy of the electromagnetic radiation used. For example, ultraviolet and visible light may induce electronic transitions, infrared light induced vibrational transitions, and microwave may induce rotational transitions. Spectrochemical properties (e.g., absorption, fluorescence, phosphorescence, or Raman scattering) are characteristic parameters of the material being examined. Because spectrochemical properties (electronic, vibrational and rotational properties) of the material 10 and the discontinuity 20 are different, the use of the electromagnetic radiation will induce a difference in photon energy absorption, thus a difference in subsequent local heating and a resulting enhanced contrast in acoustic properties between the material 10 and the discontinuity 20.

In one embodiment, the electromagnetic energy is modified so as to create variations in exposure. For example, a gate 112 may be used to create a train of pulses 114 of electromagnetic energy. Typically, the frequency of the pulses is on the order of from one femtosecond to one microsecond. Similarly, the electromagnetic energy may be modulated or scanned to prevent constant exposure of the discontinuity 20 to the electromagnetic radiation.

In one embodiment, the electromagnetic radiation is pulsed and the acoustic receiver 120 employs gated detection. In another embodiment, the electromagnetic radiation is modulated and the acoustic receiver 120 employs phase sensitive detection. In one embodiment, the source 110 could also employ a multi-photon process.

An acoustic transmitter and receiver unit 120 (e.g., an ultrasound transducer or a low frequency acoustic transducer) is employed to acquire information regarding the discontinuity 20. The transmitter and receiver unit 120 employs conventional acoustic imaging techniques and generates a signal that is received by a computer 130 to provide useful information regarding the discontinuity 20. In one example, the signal is received by an oscilloscope to provide simple detection of the discontinuity 20. In another example, as shown, the signal is processed by the computer 130 to provide a virtual image 132 of the material 10, including a virtual image 134 of the discontinuity 20.

Figure 2:
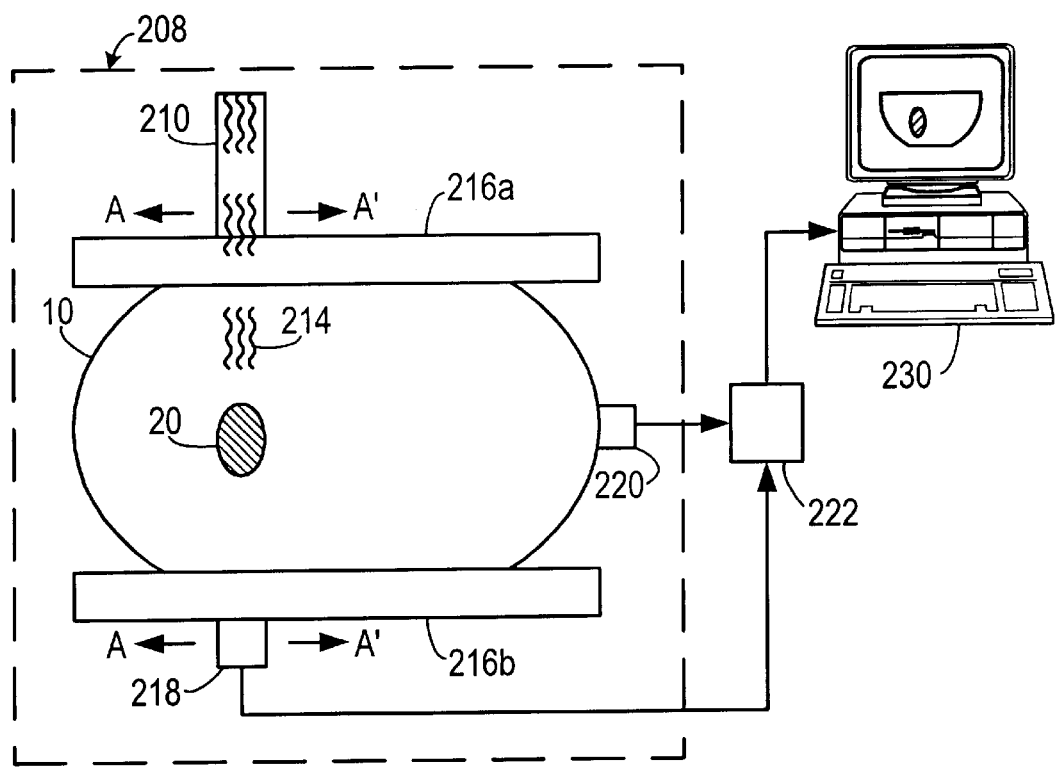
FIG. 2 is a schematic diagram of an embodiment of the invention suitable for use in mammography.

As shown in FIG. 2, an embodiment of the invention employed in mammography includes a sensing unit 208 to detect a mass 20 in a breast 10. The breast 10 is held between two plates 216a and 216b, wherein plate 216a is transparent to light and plate 216b is transparent to photo-acoustic waves (acoustic waves that are induced in a material by exposure to electromagnetic energy). The sensing unit 208 includes a light source 210 (such as a laser) that may be scanned along a transparent plate 216a and that generates light 214 that will penetrate the breast 10 to the depth of interest. Typically, shorter wavelength light (e.g., infra-red to near infra-red) is employed when examining masses nearer the surface, whereas longer wavelength light (e.g., visible or ultraviolet) is employed when examining masses deeper in the tissues.

An ultrasound transducer 220 detects the mass 20 using conventional ultrasound detection and information regarding the mass is sent from the ultrasound transducer 220 to a computer 230 for detection and further processing. A photo-acoustic receiver 218 may be added to receive waves generated as a result of the photo-acoustic effect induced by the light 214. Information from the photo-acoustic receiver 218 may then be combined with information from the ultrasound transducer 220 in a signal processing circuit 222 to provide more refined information regarding the mass to the computer 230.

A first scanner is coupled to the source 210 of electromagnetic radiation so as to cause the source to scan alone a first predefined path (e.g., A–A') and a second scanner is coupled to the photo-acoustic receiver 218 so as to cause the photo-acoustic sensor to scan along a second predefined path that is complementary to the first predefined path (e.g., A–A'). The scanners, of the type commonly known to the art, scan the source 210 and the receiver 218 over the entire area being examined.

Figure 3A:
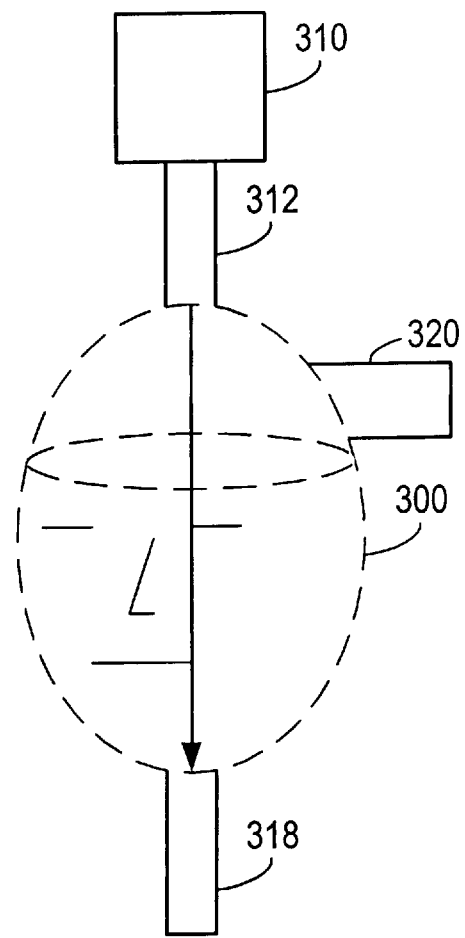
FIG. 3A is a schematic diagram of a first embodiment of the invention suitable for use in head injury-related diagnostics.

As shown in FIG. 3A, an embodiment of the invention used in detecting brain injuries employs a light source 310 and a wave guide 312 (such as an optical fiber) to transmit light to the head 300 of an individual. A low-frequency acoustic transmitter/receiver unit 320 is used to receive information regarding the brain. Low-frequency acoustic energy (e.g., using acoustic waves having a frequency of approximately or less than 1 MHz) may be employed in this embodiment because it is more likely to penetrate the scull. A photo-acoustic sensor 318 may also be employed to retrieve additional information from the patient's head 300.

Many different geometries of receivers 320 and 318 could be employed, depending on the area of the brain being examined.

Figure 3B:
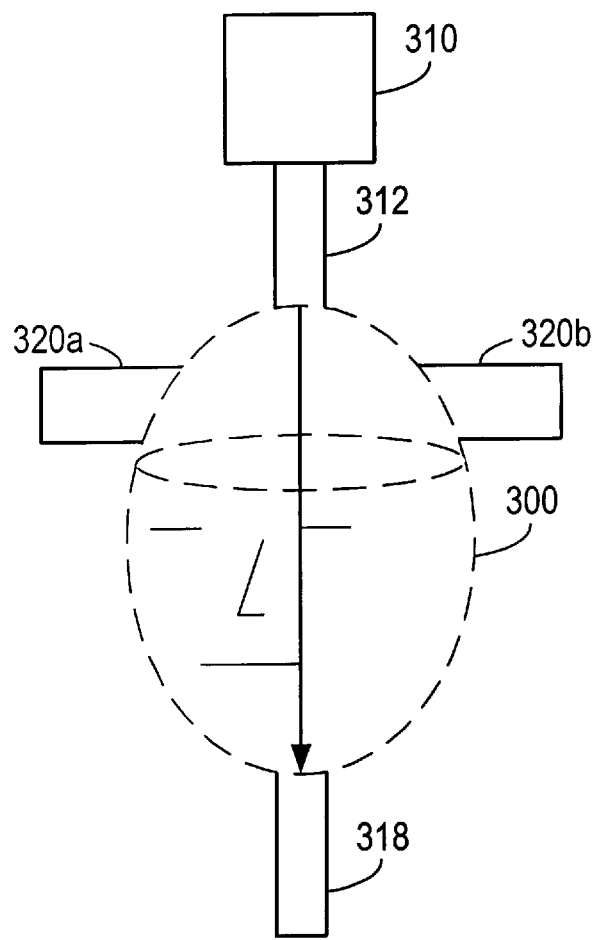
FIG. 3B is a schematic diagram of a second embodiment of the invention suitable for use in head injury-related diagnostics.

In the embodiment shown in FIG. 3B, two opposite ultrasound emitter/transducer units 320a and 320b are employed for detection of interference patterns created by the two opposite ultrasound waves interfering with each other. This embodiment facilitates detection of the midline shift in the brain, as is typical in certain types of head injury or brain tumor.

Theoretical Basis for Photo-acoustic Enhancement of Ultrasound Detection

A simple mode illustrating the basis of the photo-acoustic enhancement effect on a propagating ultrasonic wave is given below. In the absence of optical illumination, the ultrasonic field, $U_0(r,t)$, obeys the wave equation $$\nabla^2 U_0(r,t) \frac{1}{c_0(r)^2} \frac{\partial^2 U_0(r,t)}{\partial t^2} = 0, \qquad (1)$$

where $c_0(r)$ is the spatially-dependent sound velocity in the tissue. The dependence of the velocity on tissue density, $\rho_0(r)$, and compressibility, $\kappa_0(r)$, is given by $$c_0(r) = 1/[\kappa_0(r)\rho_0(r)]^{1/2}$$

When intensity-modulated light is allowed to diffuse into the tissue, the light is absorbed, converted to heat and, due to thermal expansion, produces a temporal modulation of the tissue density at the same frequency. We write this as $\rho(r,t)=\rho(r)[1+\epsilon(t)]$, where $\epsilon(t)$ represents the time-varying density perturbation. The temporal variation, $\epsilon(t)$, could be sinusoidal or a periodic pulse train. Assuming $\epsilon(t)$ varies much more slowly than the ultrasonic oscillation, Eq. (1) can be modified to read $$\nabla^2 U(r,t) \frac{1}{c(r,t)^2} \frac{\partial^2 U(r,t)}{\partial t^2} = 0. \qquad (2)$$

Substituting $c(r,t)^2 = \kappa_0(r)\rho(r,t) = \kappa_0(r)\rho_0(r)[1+\epsilon(t)] = c_0(r)^2[1+\epsilon(t)]$ into Eq. (2) gives $$\nabla^2 U(r,t) \frac{1}{c_0(r)^2} \frac{\partial^2 U(r,t)}{\partial t^2} = \frac{\epsilon(t)}{c_0(r)^2} \frac{\partial^2 U(r,t)}{\partial t^2}. \qquad (3)$$

Now letting $U(r,t)=U_0(r,t)+u(r,t)$, where $u(r,t)$ is the perturbation of the field $U(r,t)$ due to the density modulation $\epsilon(t)$, substituting Eq. (3), using Eq. (1) and dropping terms second order in the small quantities u and $\epsilon$, we obtain:

$$\nabla^2 u(r,t) \frac{1}{c_0(r)^2} \frac{\partial^2 u(r,t)}{\partial t^2} = \frac{\epsilon(t)}{c_0(r)^2} \frac{\partial^2 U_0(r,t)}{\partial t^2}. \qquad (4)$$

For the case of a cw ultrasonic wave of frequency $f_u$, we have $\omega=2\pi f_u$, $U_0(r,t)=U_0(r)\exp(i\omega t)$ and $u(r,t)=u(r)\exp(i\omega t)$, and Eq. (4) reduces to $$\nabla^2 u(r)+k_0^2(r)u(r)=\epsilon(t)k_0^2(r)U_0(r), \qquad (5)$$

where $k_0(r)=\omega/c_0(r)$. Using standard techniques, $u(r)$ can be expressed explicitly in integral form:

$$u(r)=U_0(r)+\epsilon(t)\iiint g(r|r')k_0^2(r')U_0(r')d^3r', \qquad (6)$$

where $g(r|r')$ is a Green's function. Note that only the second term on the right contains the modulation dependence, $\epsilon(t)$.

By synchronous demodulation, the second term can be extracted with high sensitivity. Once this is done, standard imaging algorithms (e.g., conventional ultrasonography or more sophisticated methods such as ultrasonic diffraction tomography) can be used to solve for the tissue spatial dependence contained in the function $k_0(r)$. It is expected that an anomalous variation in tissue density and/or compressibility due to tissue pathology should reveal itself in the spatial image of $k_0(r)$. We conclude by noting that a more general model could accommodate a possible spatial dependence of the Photo-acoustic effect itself, that is, a spatial dependence on the efficiency of Photo-acoustic energy transfer that depends on molecular tissue properties. In this case, the density can be modified to read $\rho(r,t)=\rho_0(r)[1+\beta(r)\epsilon(t)]$, where the Photo-acoustic spatial variation is contained in the function $\beta(r)$. With this change, the above analysis still applies except now $k_0^2(r)$ in the integrand of Eq. (6) will be replaced by $\beta(r)k_0^2(r)$.

Theoretical Basis for Spectroscopic Enhancement of Ultrasound Detection

Molecules in tissue can absorb UV (electronic transitions), infrared (vibrational transitions), microwave (rotational transitions). Therefore, a similar Photo-acoustic enhancement effect is expected with microwave, infrared radiation, or UV and a parallel analysis can be carried out for these types of radiation. For example, if the power deposited by a microwave source in a tissue sample is modulated with time dependence, $\epsilon(t)$, then the physical tissue density will again respond with a modulation of the general from $\rho(r,t)=\rho_0(r)[1+\beta(r)\epsilon(r)]$, where $\rho_0(r)$ is the unperturbed density and represents the spatial variation in the power density of the microwave radiation. A simple model would predict that $\beta(r)$ will attenuate exponentially into the tissue, that is, $\beta(r)=\beta_0\exp(-\alpha z')$ where z denotes depth into the tissue and is the mean microwave attenuation coefficient. In this case, Eq. (6) for the cw ultrasonic response becomes $$u(r)=U_0(r)+\epsilon(t)\beta_0\iiint g(r|r')k_0^2(r')U_0(r')\exp(-\alpha z')d^2r', \quad (7)$$

where again the quantity sought is $k_0^2(r)$ which contains the diagnostically useful information. Equation (7) now shows explicitly the property that the temporal modulation of the ultrasonic signal is influenced by the exponential absorption of the microwave energy as it penetrates the tissue. A similar type of analysis should also hold for the diffusion of infrared radiation into tissue.

Here again the combination of electronic, vibrational, and or rotational absorption properties of tissue molecules with ultrasonic detection will provide an improved biomedical diagnosis tool.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. An apparatus for detecting a discontinuity in a material, comprising:
    a. a source of electromagnetic radiation having a wavelength and an intensity sufficient to induce an enhancement in contrast between a manifestation of an acoustic property in the material and of the acoustic property in the discontinuity, as compared to when the material is not irradiated by the electromagnetic radiation;
    b. an acoustic emitter capable of directing acoustic waves to the discontinuity in the material wherein the acoustic waves have a sensitivity to the acoustic property;
    c. an acoustic receiver capable of receiving the acoustic waves generated by the acoustic emitter after the acoustic wastes have interacted with the material and the discontinuity, the acoustic receiver also capable of generating a signal representative of the acoustic waves received by the acoustic receiver; and
    d. a processor, in communication with the acoustic receiver and responsive to the signal generated by the acoustic receiver, that is programmed to generate informational output about the discontinuity based on the signal generated by the acoustic receiver.

2. The apparatus of claim 1, wherein the source of electromagnetic radiation comprises a microwave source.

3. The apparatus of claim 1, wherein the source of electromagnetic radiation comprises an optical light source.

4. The apparatus of claim 3, wherein the optical light source comprises a laser.

5. The apparatus of claim 3, wherein the optical light source is collimated.

6. The apparatus of claim 1, wherein the source of electromagnetic radiation comprises a source of infrared radiation.

7. The apparatus of claim 1, wherein the source of electromagnetic radiation comprises a source of near infrared radiation.

8. The apparatus of claim 1, wherein the source of electromagnetic radiation comprises a source of ultraviolet radiation.

9. The apparatus of claim 1, wherein the source of electromagnetic radiation comprises a source of microwave radiation.

10. The apparatus of claim 1, wherein the source of electromagnetic radiation comprises a source employing a multi-photon process.

11. The apparatus of claim 1, wherein the electromagnetic radiation is pulsed.

12. The apparatus of claim 11, wherein the acoustic receiver employs gated detection.

13. The apparatus of claim 1, wherein the electromagnetic radiation is modulated.

14. The apparatus of claim 13, wherein the acoustic receiver employs phase sensitive detection.

15. The apparatus of claim 1, wherein the acoustic waves comprise ultrasound waves.

16. The apparatus of claim 1, wherein the acoustic waves comprise low-frequency acoustic waves.

17. The apparatus of claim 16, wherein the low-frequency acoustic waves have a frequency of less than 1 MHz.

18. The apparatus of claim 1, further comprising a photo-acoustic sensor.

19. The apparatus of claim 18, further comprising a first scanner coupled to the source of electromagnetic radiation so as to cause the source to scan along a first predefined path.

20. The apparatus of claim 19, further comprising a second scanner coupled to the photo-acoustic sensor so as to cause the photo-acoustic sensor to scan along a second predefined path that is complementary to the first predefined path.

21. An apparatus for detecting a mass, having a density, in a tissue, having a density, comprising:
    a. an electromagnetic radiation source capable of directing a beam of electromagnetic radiation into the tissue toward the mass, the beam having a wavelength and intensity sufficient to induce an enhancement in contrast between the density of the mass relative to the density of the tissue;
    b. an ultrasound transmitter capable of directing ultrasound waves into the tissue toward the mass;

c. an ultrasound receiver capable of receiving ultrasound waves that have interacted with the tissue and the mass; and d. a processor, responsive to the ultrasound receiver, that detects the mass based on the ultrasound waves received by the ultrasound receiver.

22. The apparatus of claim 21, wherein said beam of electromagnetic radiation is pulsed.

23. The apparatus of claim 21, wherein said beam of electromagnetic radiation is pulsed, and wherein the ultrasound receiver employs gated beam detection.

24. The apparatus of claim 21, wherein the beam of electromagnetic radiation is modulated.

25. The apparatus of claim 21, wherein the beam of electromagnetic radiation is modulated, and wherein the ultrasound receiver is phase sensitive.

26. The apparatus of claim 21, wherein the beam of electromagnetic radiation is gated, and wherein the ultraisound receiver employs gated beam detection.

27. The apparatus of claim 21, further comprising:

a. means for making the beam of radiation modulated; and b. means for making detection in the ultrasound receiver phase sensitive.

28. The apparatus of claim 21, wherein the electromagnetic radiation source comprises a light source.

29. The apparatus of claim 28, wherein the light source comprises a laser.

30. The apparatus of claim 21, electromagnetic radiation source comprises a microwave source.

31. The apparatus of claim 21, wherein the means for making the beam of light comprises a pulsing device.

32. The apparatus of claim 21, wherein the means for making the beam of light comprises a modulator.

33. A method of detecting a discontinuity in a material, comprising the steps of:

a. irradiating the material with a beam of electromagnetic radiation having an energy and an intensity sufficient to induce an enhancement in contrast between a manifestation of an acoustic property in the material and of the acoustic property in the discontinuity, as compared the contrast when the material is not irradiated by the beam;

b. irradiating the material with acoustic waves so that acoustic energy interacts with the material and the discontinuity;

c. receiving waves that have interacted with the material and the discontinuity; and d. generating an informational output about the discontinuity based on the received waves that have interacted with the material and the discontinuity.

34. A method of detecting a mass in a tissue, comprising the steps of:

a. irradiating the tissue with a beam of electromagnetic radiation having an energy and an intensity sufficient to induce an enhancement in contrast between a manifestation of an acoustic property in the tissue and of the acoustic property in the mass, as compared the contrast when the tissue is not irradiated by the beam;

b. irradiating the tissue with acoustic waves so that acoustic energy interacts with the tissue and the mass;

c. receiving waves that have interacted with the tissue and the mass; and d. generating an informational output about the mass based on the received waves that hive interacted with the tissue and the mass.

* * * * *